US00PP31842P3

(12) United States Plant Patent
van Geest

(10) Patent No.: US PP31,842 P3
(45) Date of Patent: Jun. 2, 2020

(54) ***ALOCASIA* PLANT NAMED 'ESAL1801'**

(50) Latin Name: *Alocasia zebrina*
Varietal Denomination: ESAL1801

(71) Applicant: J. Van Geest Holding B.V., Gravenzande (NL)

(72) Inventor: Jan van Geest, Gravenzande (NL)

(73) Assignee: J. Van Geest Holding B.V., Gravenzande (NL)

( * ) Notice: Subject to any disclaimer, the term of this patent is extended or adjusted under 35 U.S.C. 154(b) by 0 days.

(21) Appl. No.: 16/501,279

(22) Filed: Mar. 16, 2019

(65) Prior Publication Data

US 2020/0113099 P1 Apr. 9, 2020

(30) Foreign Application Priority Data

Oct. 9, 2018 (QZ) ..... PBR 2018/2547

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 6/10
See application file for complete search history.

*Primary Examiner* — Anne Marie Grunberg
(74) *Attorney, Agent, or Firm* — Samuel R. McCoy, Jr.

(57) ABSTRACT

'ESAL 1801' is a distinctive cultivar of *Alocasia* plant which is characterized by the combination of large dark green foliage with green venation, slightly to moderately bullate foliage with raised veins, a lamina which is held upright to horizontal relative to the petiole, and the stability of all characteristics from generation to generation.

3 Drawing Sheets

Latin name of the genus and species: The Latin name of the genus and species of the novel variety disclosed herein is *Alocasia zebrina*.

Variety denomination: The inventive variety of *Alocasia* disclosed herein has been given the variety denomination 'ESAL1801'.

CROSS REFERENCE TO RELATED APPLICATIONS

This application claims priority to the Community Plant Variety Rights application number 2018/2547, filed Oct. 9, 2018 which is herein incorporated by reference.

BACKGROUND OF THE INVENTION

Parentage: 'ESAL1801' originated as a naturally occurring, whole-plant mutation of an unnamed *Alocasia zebrina* plant (not patented). In the summer of 2017, the inventor discovered the mutation at his commercial greenhouse in Gavenzande, The Netherlands, growing amongst a cultivated population of unnamed *Alocasia zebrina* plants. The mutation was noted for its large foliage and near-black leaf petiole and was subsequently isolated for further evaluation in order to confirm the distinctness and stability of the characteristics first observed. Upon confirmation of distinctness and stability, 'ESFIBE1801' was selected for commercialization.

Asexual Reproduction: Asexual reproduction of 'ESFIBE1801', by way of vegetative cuttings, was first initiated in the summer of 2017 at a commercial greenhouse in Gavenzande, The Netherlands. Through five subsequent generations, the unique features of this cultivar have proven to be stable and true to type.

SUMMARY OF THE INVENTION

The cultivar 'ESAL1801' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'ESAL1801'. These characteristics in combination distinguish 'ESAL1801' as a new and distinct *Alocasia* cultivar:

1. *Alocasia* 'ESAL1801' exhibits large, broadly sagitate foliage with an apiculate apex; and
2. *Alocasia* 'ESAL1801' exhibits dark green foliage with prominent raise veins that are also colored green; and
3. *Alocasia* 'ESAL1801' exhibits slightly to moderately bullate foliage with raised, prominent veins; and
4. *Alocasia* 'ESAL1801' exhibits a lamina which is held upright to horizontal, relative to the petiole.

BOTANICAL DESCRIPTION OF THE PLANT

Figure 1:
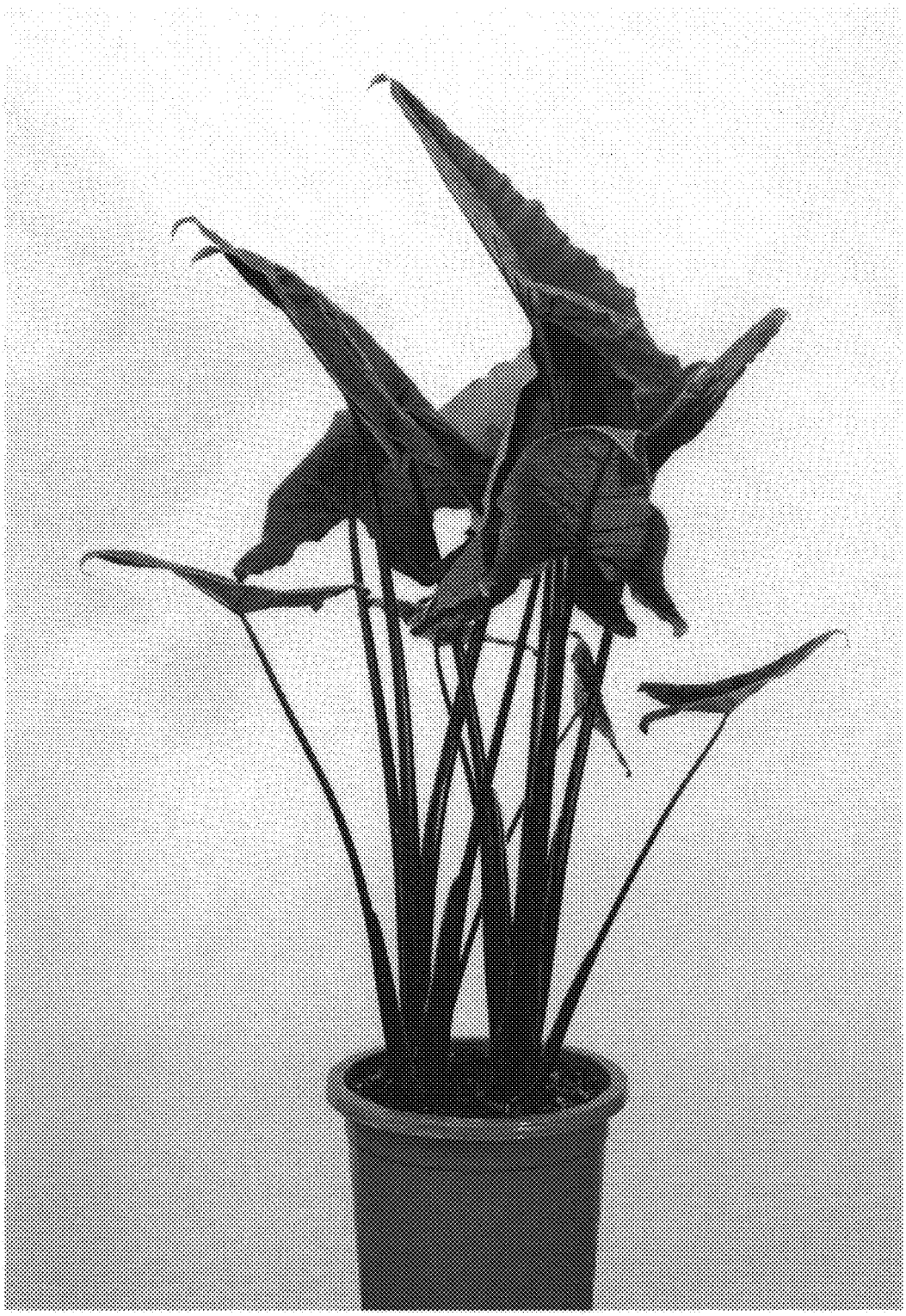
FIG. 1 illustrates, as nearly true as it is reasonably possible to make the same in color photographs of this type, two exemplary plants of 'ESAL1801' grown in a commercial greenhouse in Gavenzande, the Netherlands. These plants are approximately 25 weeks old, shown planted in a 28 cm container.
Figure 2:
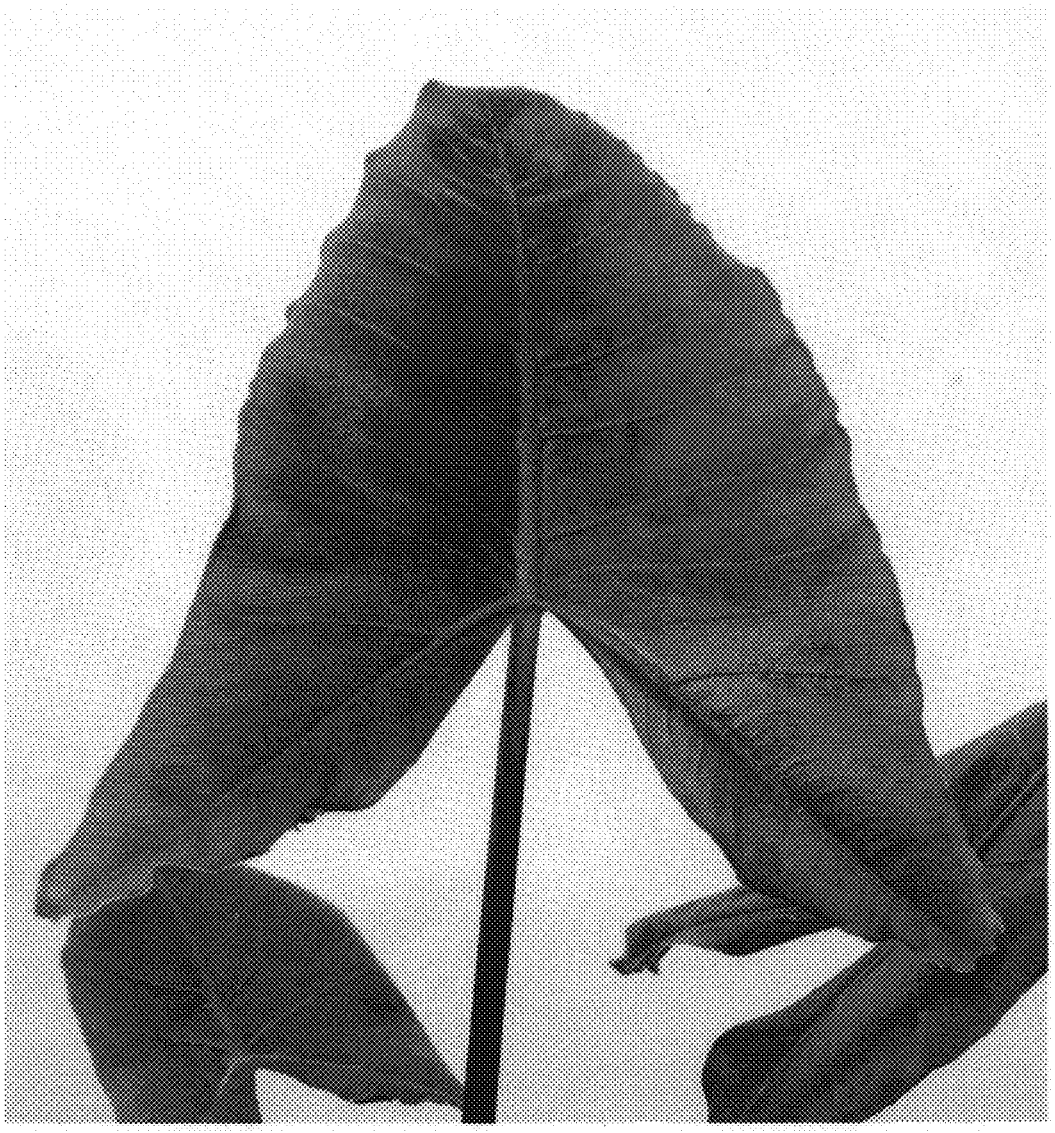
FIG. 2 illustrates, as nearly true as it is reasonably possible to make the same in color photographs of this type, the typical mature foliage of 'ESAL1801'.
Figure 3:
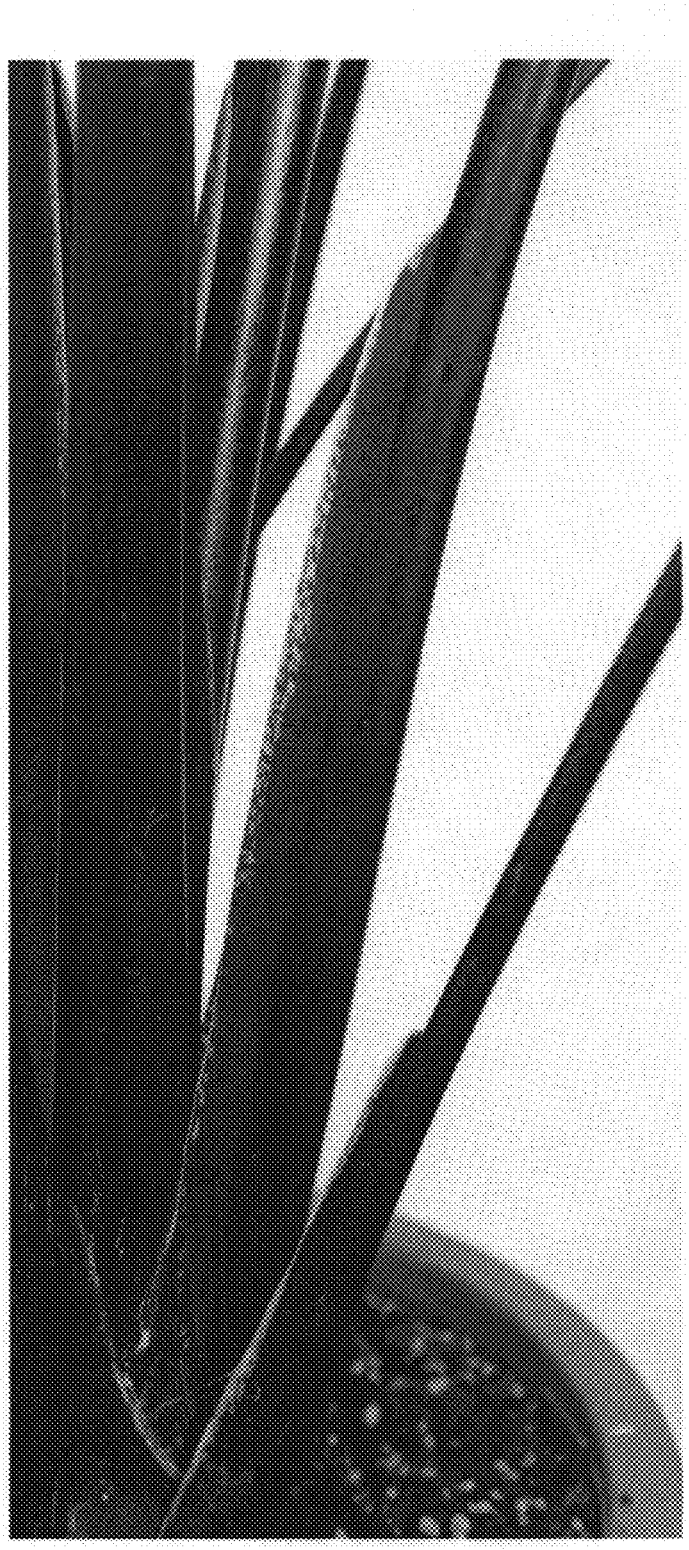
FIG. 3 illustrates, as nearly true as it is reasonably possible to make the same in color photographs of this type, the typical petiole of 'ESAL1801'.

The following observations and measurements made in September of 2018 describe averages from two 26 week-old 'ESAL1801' plants grown in a 28 cm nursery container at a greenhouse in Gavenzande, the Netherlands. Plants were produced in a greenhouse with 50 percent shade covering, ebb and flood irrigation tables, no supplemental fertilizer, and no preventative or pest control measures utilized.

Those skilled in the art will appreciate that certain characteristics will vary with older or, conversely, with younger plants. 'ESAL1801' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'ESAL1801' and a comparison with the parent plant and most similar commercial comparator are provided below.

Plant description:

*Growth habit*.—Herbaceous perennial with a broad, upright growth habit; leaves growing from a basal clump.

*Plant shape*.—Broad obovate.

*Height from soil level to top of foliar plane*.—111.0 cm.

*Plant spread*.—101.8 cm.

*Growth rate*.—Fast.

*Plant vigor*.—Very vigorous.

*Propagation type*.—Stem cuttings.

*Time to produce a rooted cutting*.—Approximately 40 days to produce a rooted cutting at approximately 25 degrees Celsius.

*Time to produce a finished plant*.—Approximately 20 weeks to produce a marketable finished plant in a 17 cm pot.

*Disease and pest resistance or susceptibility*.—Neither susceptibility nor resistance to pests and diseases common to either *Alocasia* have been observed.

*Environmental tolerances*.—Adapt to temperatures as low as 5 degrees Celsius and as high as 40 degrees Celsius; moderate to high tolerance to rain; low tolerance to wind.

Roots:

*General*.—Moderately dense, moderately branched rooting; roots are fleshy.

*Distribution in the soil profile*.—Shallow to moderately deep.

*Diameter of roots*.—5.0 mm on average.

*Texture*.—Smooth; no root hairs.

*Color*.—White, nearest to RHS 155C.

Foliage:

*Quantity*.—7 leaves per clump.

*Arrangement*.—Alternate.

*Attachment*.—Petiolate.

*Division*.—Simple.

*Lamina*.—Attitude — Ranging from near horizontal to slightly pendulous. Shape — Broad sagitate. Length — 45.9 cm, excluding the petiole. Width — 29.8 cm. Apex — Apiculate. Base — Obtuse. Aspect — Slightly to moderately concave; curled downward at the apex. Margins — Entire and slightly angular; slightly to moderately undulate. Texture and luster, adaxial surface — Slightly to moderately bullate, glabrous and moderately glossy. Texture and luster, abaxial surface — Slightly to moderately bullate, glabrous and moderately glossy. Color — Juvenile foliage, adaxial surface — Green, nearest to in between RHS 137A and 143A. Juvenile foliage, abaxial surface — Yellow-green, nearest to RHS 147D. Mature foliage, adaxial surface — Green, nearest to in between RHS NN137A and 139A. Mature foliage, abaxial surface — Nearest to in between green and yellow-green, RHS 138B and 147B. Venation — Pattern — Pinnate. Color, adaxial surfaces — Greyed-green, nearest to RHS 189A. Color, abaxial surface — Yellow-green, in between RHS 146A and 147B.

*Petiole*.—Attitude — Upright and slightly outward. Strength — Very strong. Length — 76.9 cm. Diameter — 2.1 cm. Texture and luster, adaxial surface — Smooth, glabrous and glossy. Texture and luster, abaxial surface — Smooth, glabrous and glossy. Color, adaxial surface — Black, nearest to RHS 202A, and lightly suffused with yellow green, nearest to RHS 147A. Color, abaxial surface — Black, nearest to RHS 202A, and lightly suffused with yellow green, nearest to RHS 147A. Sheath — Shape — Deltoid. Length — 34.9 cm. Width — 1.7 cm. Margin — Entire; not undulated. Texture and luster — Smooth, glabrous and glossy. Color — Black, nearest to RHS 202A, and lightly suffused with yellow green, nearest to RHS 147A; margined with a mixture of yellow-green and green-white, nearest to RHS 144C and 157B.

Inflorescence: To date, 'ESAL1801' has not flowered.

COMPARISONS WITH THE PARENT PLANTS

Plants of the new cultivar 'ESAL1801' differ from the parent, an unnamed *Alocasia zebrina* plant (not patented), in the characteristics described in Table 1 below.

TABLE 1

| Characteristic | 'ESAL1801' | The parent |
|---|---|---|
| General coloration of the petiole. | Black. | Green with light greyed-yellow to light brown striped. |

COMPARISONS WITH THE CLOSEST KNOWN COMPARATOR

Plants of the new cultivar 'ESAL1801' differ from the closest known commercial comparator, *Alocasia* sp. 'Polly' (not patented), in the following characteristics described in Table 2 below.

TABLE 2

| Characteristic | 'ESAL1801' | 'Polly' |
|---|---|---|
| General coloration of the petiole. | Black. | A mixture of greyed-yellow and light brown. |
| Foliage shape. | Moderately sagitate; basal lobes less pronounced. | Strongly sagitate with prominent basal lobes. |
| General coloration of the foliage. | Green with green venation. | Green with prominent white venation. |

That which is claimed is:

1. A new and distinct variety of *Alocasia* plant named 'ESAL1801', substantially as described and illustrated herein.

* * * * *